United States Patent
Huffman et al.

(10) Patent No.: US 8,085,075 B2
(45) Date of Patent: Dec. 27, 2011

(54) METHOD AND SYSTEM FOR DIAGNOSTIC IMAGING USING A DIGITAL PHASE LOCKED LOOP

(75) Inventors: Nathanael Dale Huffman, Sussex, WI (US); Jason Stuart Katcha, Whitefish Bay, WI (US); Phil E. Pearson, Jr., Hartland, WI (US)

(73) Assignee: General Electric Comapany, Schenectady, NY (US)

( * ) Notice: Subject to any disclaimer, the term of this patent is extended or adjusted under 35 U.S.C. 154(b) by 230 days.

(21) Appl. No.: 11/894,003

(22) Filed: Aug. 16, 2007

(65) Prior Publication Data
US 2009/0045859 A1    Feb. 19, 2009

(51) Int. Cl.
*H03L 7/06* (2006.01)
(52) U.S. Cl. .......................... 327/159; 378/4
(58) Field of Classification Search ............. 378/4, 15, 378/19; 327/147, 156; 375/376
See application file for complete search history.

(56) References Cited

U.S. PATENT DOCUMENTS

| | | | | |
|---|---|---|---|---|
| 4,855,683 A | * | 8/1989 | Troudet et al. | 327/159 |
| 5,175,754 A | * | 12/1992 | Casey et al. | 378/4 |
| 6,028,412 A | * | 2/2000 | Shine et al. | 318/696 |
| 6,574,301 B1 | * | 6/2003 | Jansen | 378/20 |
| 2005/0078783 A1 | * | 4/2005 | Okita | 375/376 |
| 2006/0033589 A1 | * | 2/2006 | Partridge et al. | 331/154 |
| 2007/0280405 A1 | * | 12/2007 | Krumme et al. | 378/4 |

* cited by examiner

*Primary Examiner* — Hoon Song
(74) *Attorney, Agent, or Firm* — Dean D. Small; The Small Patent Law Group

(57) ABSTRACT

A method and apparatus are provided for minimizing output pulse jitters in a phase locked loop. The method includes pre-setting the digital phase locked loop to a desired frequency, locking the digital phase locked loop to the desired frequency to generate an output signal, and filtering the output signal of the digital phase locked loop to maintain undesirable jitter to an acceptable range. In one embodiment, the apparatus is a medical imaging device. In another embodiment, the apparatus is a baggage imaging device.

17 Claims, 6 Drawing Sheets

System Block Diagram with remainder fix and trigger Interpolation

METHOD AND SYSTEM FOR DIAGNOSTIC IMAGING USING A DIGITAL PHASE LOCKED LOOP

BACKGROUND OF THE INVENTION

The invention relates generally to methods and apparatus for diagnostic imaging, and more particularly to a trigging apparatus that responds to changing input frequencies to allow a digital phase lock loop to rapidly lock to a desired output frequency.

In certain known diagnostic imaging systems, such as CT imaging systems, an x-ray source transmits x-ray beams towards an object of interest. The x-ray beams pass through the object being imaged, such as a patient or baggage. The beams, after being attenuated by the object, impinge upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. Attenuation measurements from the detectors are acquired separately for each detector element and collectively define a projection data set or transmission profile.

The x-ray source and the detector array are rotated on a gantry within an imaging plane around the object to be imaged such that the angle at which the x-ray beam intersects the object constantly changes. A group of x-ray attenuation measurements, e.g., projection data set, from the detector array at one gantry angle is referred to as a "view." A "scan" of the object comprises a set of views made at different gantry angles, or view angles, during one revolution of the x-ray source and detector. The projection data sets are processed to construct images that correspond to two-dimensional slices taken through the object at various angles.

Conventional CT medical imaging and baggage scanning systems include a triggering apparatus for triggering the acquisition of projections. The triggering apparatus may use an encoder to provide a predetermined number of pulses per gantry revolution. A phase locked loop (PLL) may be used to multiply and filter the encoder signals to provide a stable output frequency. For instance, existing CT systems may use an analog PLL that includes a digital filter on the input to stabilize input frequency parameters to provide filtering to reduce or maintain the jitter of an output signal within an acceptable range. Jitter is typically defined as an irregular random movement of the output signal above or below a desired frequency level. Analog PLLs with a external digital filter are typically slow to respond to variations in input frequency to provide adequate output filtering. To accurately acquire projections, the rate of rotational speed change of the CT gantry is limited by the response time of the PLL, limiting the ability to rapidly change rotational speeds which is desirable for diagnostic and image reconstruction purposes. Furthermore, typical commercial systems limit the number of output pulses per gantry rotation from the PLL to a defined set of values, e.g., three values. Moreover, communications errors between the PLL input source, for instance, an encoder and the PLL may cause a scan to abort because of a missing or jittered acquisition trigger.

It is desirable to provide a diagnostic imaging system, for example, a CT system that has a trigger interpolation system that provides increased system stability to non-ideal events such as noise, communication errors and impaired electronic functionality. It would be further desirable for the system to be able to specify triggers per each gantry rotation at any arbitrary number while maintaining output jitter within a predetermined acceptable range. It is also desirable to provide a CT system that has the ability to interpolate digital acquisition system (DAS) triggers to allow the CT system to avoid aborting a scan by being able to continue scanning when an intermittent error or instantaneous error occurs. The PLL may be set to a desired frequency and in the event of a missing or late input pulse it would be desirable to interpolate the output pulses to stabilize the PLL and prevent additional unwanted jitter from being introduced into the output signal

BRIEF DESCRIPTION OF THE INVENTION

In one embodiment, a method is provided for minimizing output pulse jitters in a phase locked loop. The method includes pre-setting the digital phase locked loop to a desired frequency, locking the digital phase locked loop to the desired frequency to generate an output signal, and filtering the output signal of the digital phase locked loop to maintain undesirable jitter to an acceptable range.

The method further includes interpolating a trigger value in real-time to continue a scan when a trigger has been missed, delayed, or fails. The failure may result from noise, an intermittent error, an instantaneous error, or a communications error, such as the phase lock loop not receiving an encoder pulse. The trigger value is based on either a frequency of previously generated digital acquisition triggers or a history of generated encoder pulses over a predetermined period of time.

In another embodiment, a medical imaging apparatus having an x-ray source and a detector array configured to minimize output signal jitter is provided. The apparatus includes a gantry coupled to the x-ray source, a detector array, an encoder, and a phase locked loop. The gantry configured to rotate within a scan plane around an object. The encoder coupled to the gantry, and generating a signal for each gantry rotation. The phase locked loop system coupled to the encoder. The phase locked loop is configured to compare the input signal from the encoder to a desired predetermined value and accept a value to dynamically correct the input signal to the desired output signal value, the output signal having minimal jitter.

In another embodiment, a baggage imaging apparatus having an x-ray source and a detector array configured to minimize output signal jitter is provided. The apparatus includes a gantry coupled to the x-ray source, a detector array, an encoder, and a phase locked loop. The gantry configured to rotate within a scan plane around an object. The encoder coupled to the gantry, and generating a signal for each gantry rotation. The phase locked loop system coupled to the encoder. The phase locked loop is configured to compare the input signal from the encoder to a desired predetermined value and accept a value to dynamically correct the input signal to the desired output signal value, the output signal having minimal jitter.

DETAILED DESCRIPTION OF THE INVENTION

Figure 1:
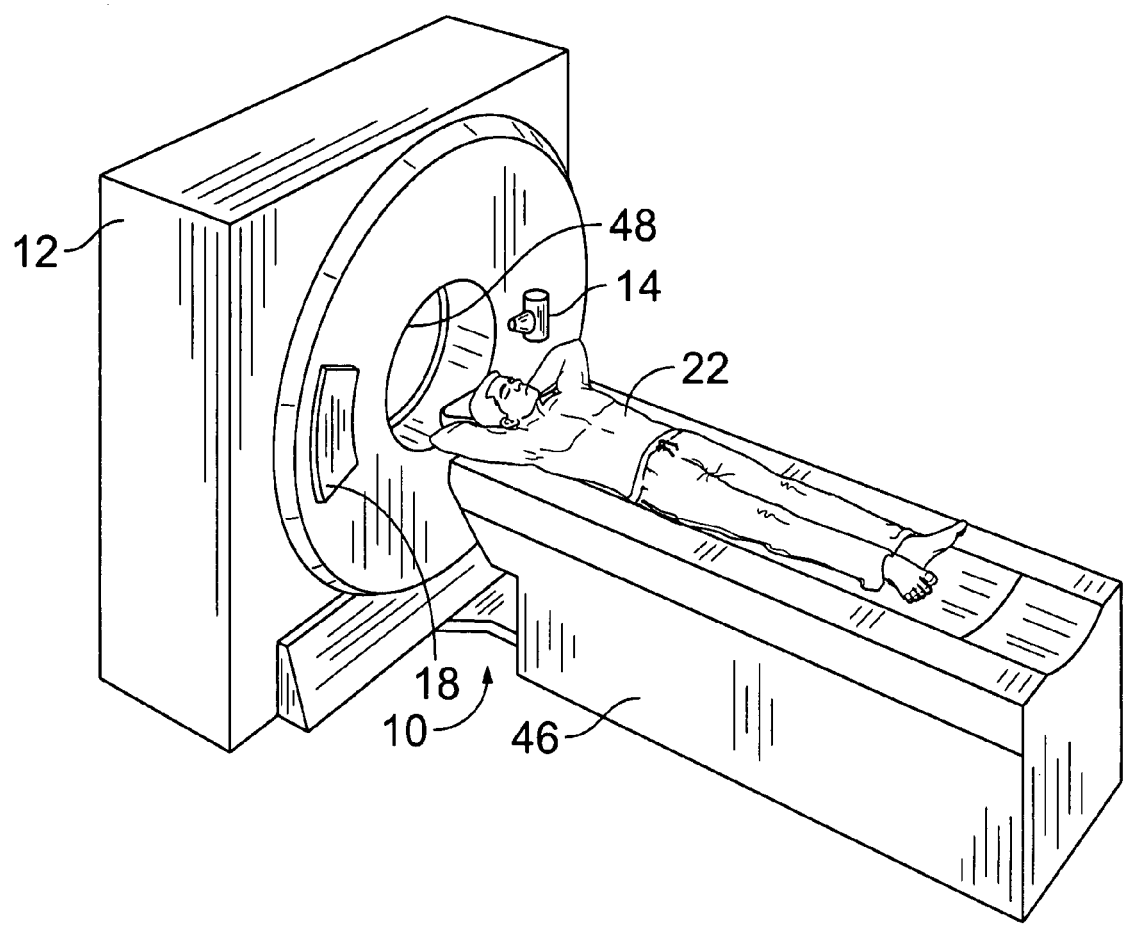
FIG. 1 illustrates a CT imaging system constructed in accordance with an embodiment of the present invention.

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

In this document, the terms "a" or "an" are used, to include one or more than one. In this document, the term "or" is used to refer to a nonexclusive or, unless otherwise indicated. In addition, as used herein, the phrase "pixel" also includes embodiments of the present invention where the data is represented by a "voxel". Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan-shaped beam that is collimated to lie within an X-Y plane of a Cartesian coordinate system and generally referred to as an "imaging plane." The x-ray beam passes through an object being imaged, such as a patient or baggage. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient or the baggage is moved while the data for a prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighting algorithms that weight the acquired data as a function of view angle and detector channel index. Specifically, prior to a filtered backprojection process, the data is weighted according to a helical weighing factor, which is a function of both the gantry angle and the detector angle. The weighted data is then processed to generate CT numbers and to construct an image that corresponds to a two-dimensional slice taken through the object.

Figure 2:
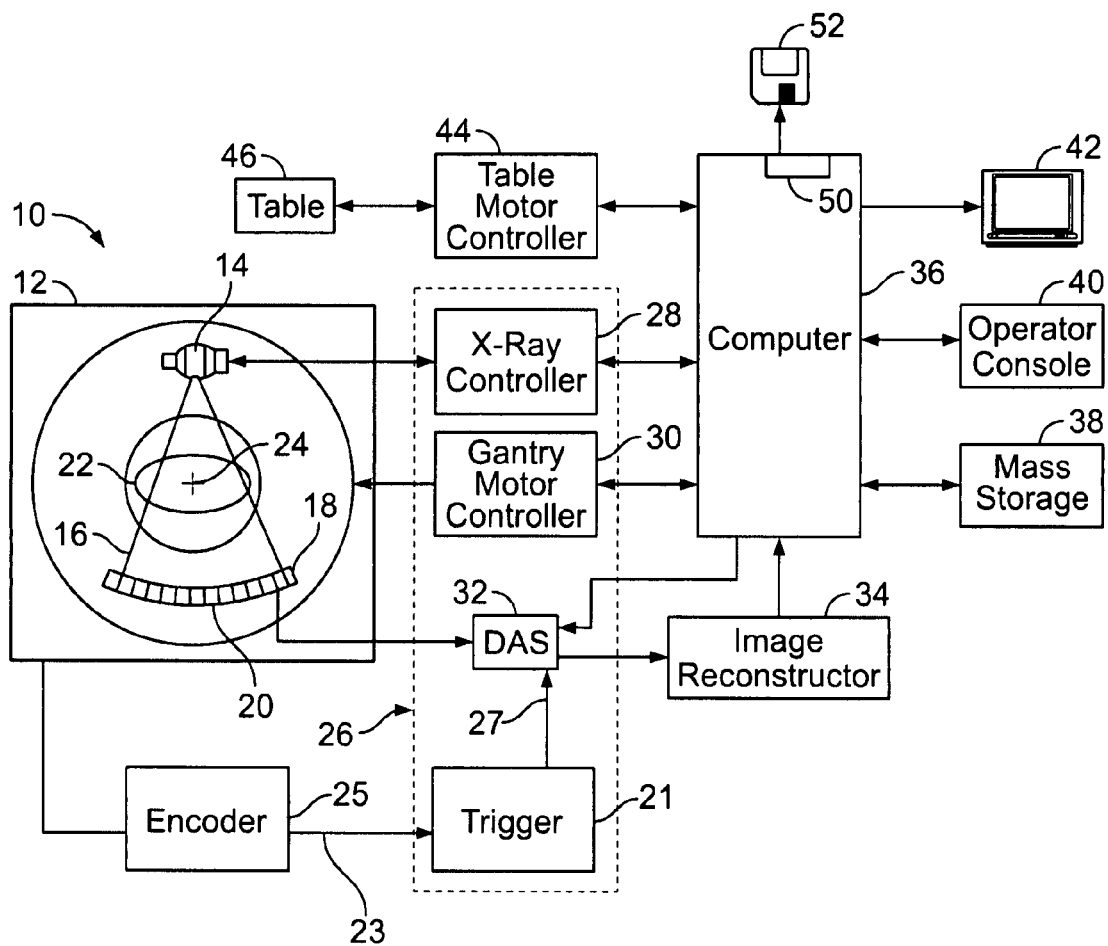
FIG. 2 is a block diagram of a CT imaging system formed in accordance with an embodiment of the present invention.

Referring to FIGS. 1 and 2, a computed tomography (CT) imaging system 10 is shown that includes a gantry 12 for a CT scanner. Gantry 12 has a radiation source such as an x-ray source 14 that projects a beam of radiation such as x-rays 16 toward a detector array 18 on the opposite side of gantry 12. Detector array 18 is formed by a plurality of detector rows (not shown) including a plurality of detector elements 20 that together sense the projected x-rays that pass through an object 22, for example a medical patient or a piece of luggage, between array 18 and source 14. Detector array 18 may be fabricated in a single slice or multi-slice configuration. Each detector element 20 produces an electrical signal that represents the intensity of an impinging radiation (e.g., x-ray) beam and hence can be used to estimate the attenuation of the beam as the beam passes through object or patient 22. During a scan to acquire x-ray projection data, gantry 12 and the components mounted thereon rotate about a center of rotation 24. FIG. 2 shows only a single row of detector elements 20 (e.g., a detector row). However, multi-slice detector array 18 may include a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32, in control mechanism 26, samples analog data from detector elements 20 and converts the data to digital signals using an encoder 25 for subsequent processing, and a trigger 21 that receives an encoder signal 23 from the encoder 21. The trigger 21 produces a projection acquisition signal 27 that commands the DAS 32 to sample the detected image data from the detector. In one embodiment the trigger 21 may include a digital phase locked loop that may be configured to rapidly change a triggering output signal based on a rapid change in gantry rotational speed, (e.g., speed change between heartbeats), where the output signal has minimal jitter. The DAS 32 outputs projection data sets including attenuation measurements obtained at particular gantry rotation angles (e.g., view angles). As the gantry 12 rotates a plurality of views may be acquired during a single rotation. A single rotation being one complete 360 degree revolution of the gantry 12. Each view has a corresponding view angle and thus, a particular location on the gantry 12. For instance, for each gantry rotation, there may be 1,000 views, where a view angle is 0.36 degrees.

The projection data sets correspond to a particular view angle as the gantry 12 rotates about a patient 22. A group of projection data sets form a complete scan of the patient 22. For instance, a complete scan of a region of interest of the patient 22 may include a complete set of projection data sets (e.g., multiple projection data sets corresponding to multiple views during a single complete rotation of gantry 12). An image reconstructor 34 receives sampled and digitized x-ray data from DAS 32 and performs high-speed image reconstruction. The reconstructor 34 may produce data sets that represent volumetric data sets or image slices through patient 22. The reconstructed image is output by the image reconstructor 34 and applied as an input to a computer 36, which stores the image in a storage device 38 (e.g., memory). The image reconstructor 34 can be specialized hardware or computer programs executing on computer 36.

Computer 36 also receives commands and scanning parameters from an operator via console 40 that has a keyboard or other suitable input device. An associated cathode ray tube display 42 or other suitable display device allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). In some configurations, computer 36 and/or image reconstructor 34 is/are programmed to perform functions described herein. Also, as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (e.g., a stationary detector with a rotating x-ray source) and fifth generation CT systems (e.g., a stationary detector and an x-ray source). Additionally, it is contemplated that the benefits of the invention accrue to imaging modalities other than CT, for example, MRI, SPECT, and PET as well as CT baggage scanners.

Thus, each projection data set is associated with a particular table position and gantry rotation angle at which the projection data set was acquired. Each corresponding projection data set is stored in memory 38. The memory 38 stores a group of projection data sets for a complete scan or examination of patient 22, a group of projection data sets that correspond to a volumetric area of the patient 22, as well as projection data sets used to update an image.

Figure 3:
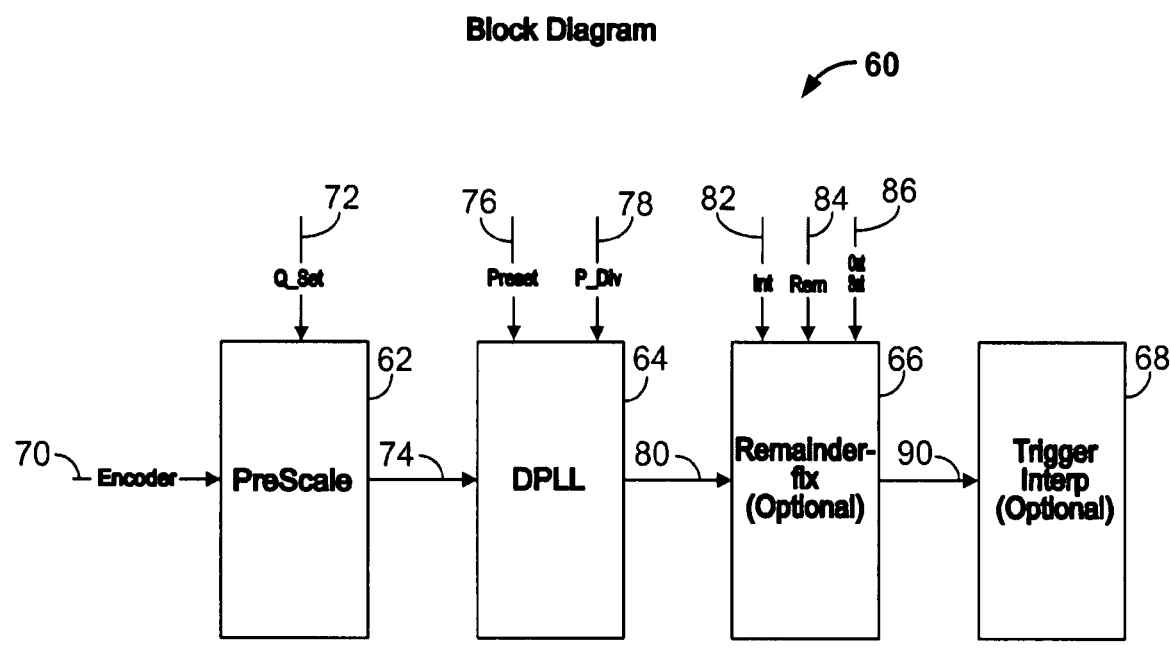
FIG. 3 is a block diagram of a digital trigger interpolation system constructed in accordance with an embodiment of the present invention.

FIG. 3 illustrates a block diagram of a digital trigger interpolation system 60 constructed in accordance with an embodiment of the present invention. System 60 includes a PreScale module 62, a digital phase locked loop 64, a remainder module 66, and a trigger interpolation module 68. The PreScale module 62 receives, as input from the encoder 25 (shown in FIG. 2), a series of pulses 70. The PreScale module 62 samples the input pulses 70, to create a scaled pulse train. The frequency of the scaled pulse train may be selected by a Q-set value 72, which either multiplies or divides the initial encoder pulse train 70. For instance, multiplication may be performed using a high-speed system clock source and a digital divider, as described below. The output of the PreScale module 62 is a scaled pulse train 74, which is input into the digital phase locked loop 64 (DPLL). The DPLL 64 further receives a Preset signal 76 and a P-Div signal 78 as inputs. The Preset signal 76 is generated by a processor external to the DPLL 78 and may be used to seed a change in trigger output frequency as the result of a change in the speed of a motor (not shown) by setting a desired accumulator value. The P_Div signal 78 may be used to set a value to divide the output feedback of the DPLL 64, as described in detail below. The DPLL 64 responds to changing input frequencies to produce a stable output signal 80 having minimal jitter. The output of the DPLL 64 may be an arbitrary number of pulses based on a pre-determined number of input pulses from the encoder 70. Optionally, the output 80 of the DPLL 64 may be input to a remainder-fix module 66. The remainder-fix module 66 receives an "Int" signal 82, a "Rem" signal 84, and an "Out Set" signal 86. The Int signal 82 may set the number of counts that correspond to an integer portion of a division operation (e.g., INTEGER(input pulses/rotation)(Output pulses/rotation)), as described in detail below. The Rem signal 84 may set the number of counts which correspond to the portion of a remainder operation (e.g., REM(input pulses/rotation)/(Output pulses/rotation)). The Out Set signal 88 may set the desired number of rotations per second. Furthermore, the output of the remainder-fix module 66 may be input to a trigger interpolator module 68, which is described in detail below.

Figure 4:
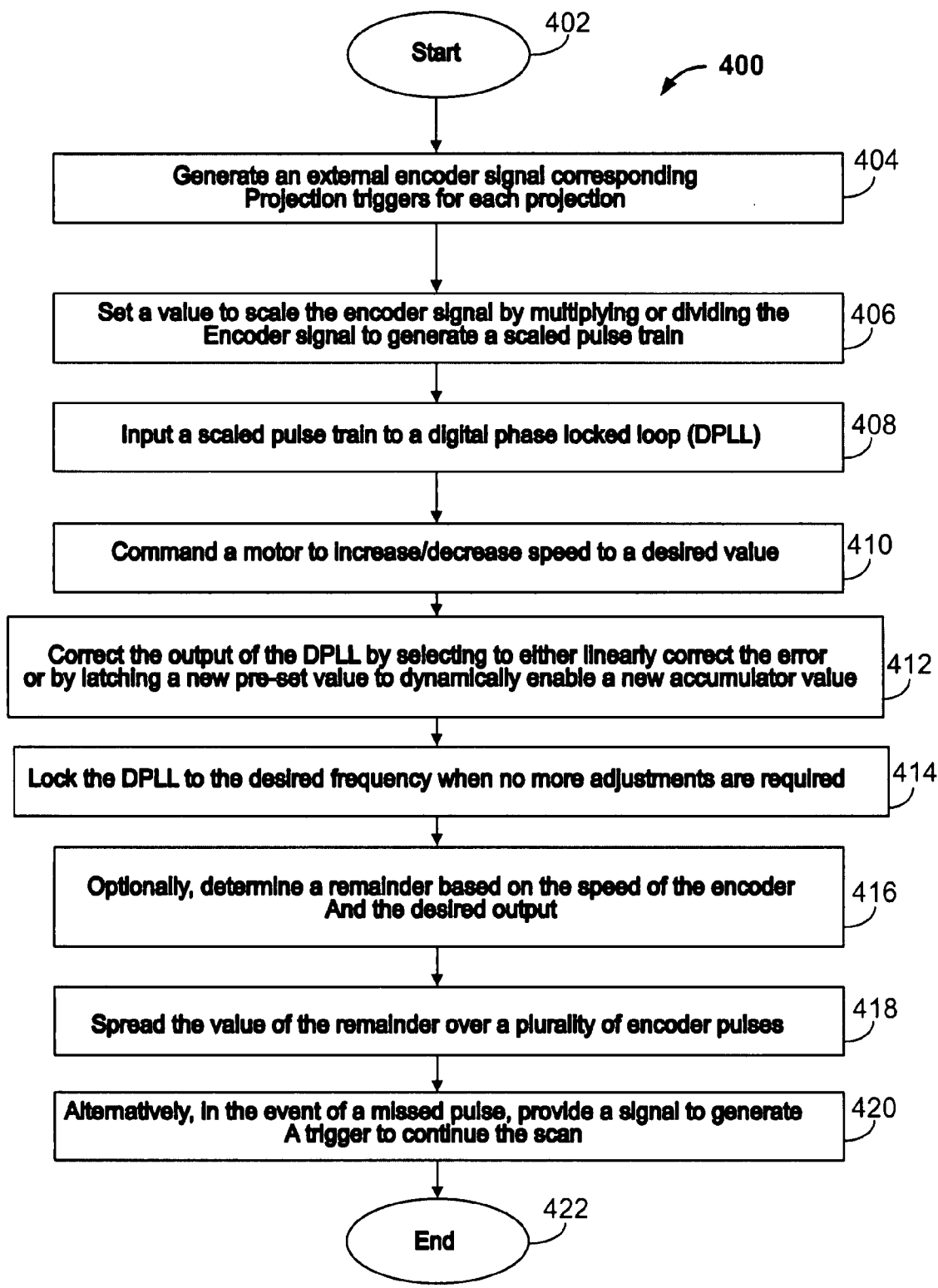
FIG. 4 is a flow diagram of a series of process steps performed in accordance with an embodiment of the present invention.

FIG. 4 illustrates a flow diagram of a series of steps for a process 400 performed in accordance with an embodiment of the present invention. The process 400 may be implemented by one or more devices and apparatus discussed above in connection with FIGS. 1-3. At 402, the process commences by initiating the medical apparatus to cause the gantry 12 to start revolving around a patient 22.

At 404 as the gantry 12 rotates, an encoder 25 (shown in FIG. 2) generates an encoder signal 23 corresponding to projection triggers to be produced by trigger module 21 for each projection. The encoder signal 23 may be a plurality of pulses. The pulses may be equally spaced having the same interval between each pulse. Alternatively, the pulses may be separated by intervals having varying length of times due to mechanically or electrically induced jitter or change in system speed.

Figure 5:
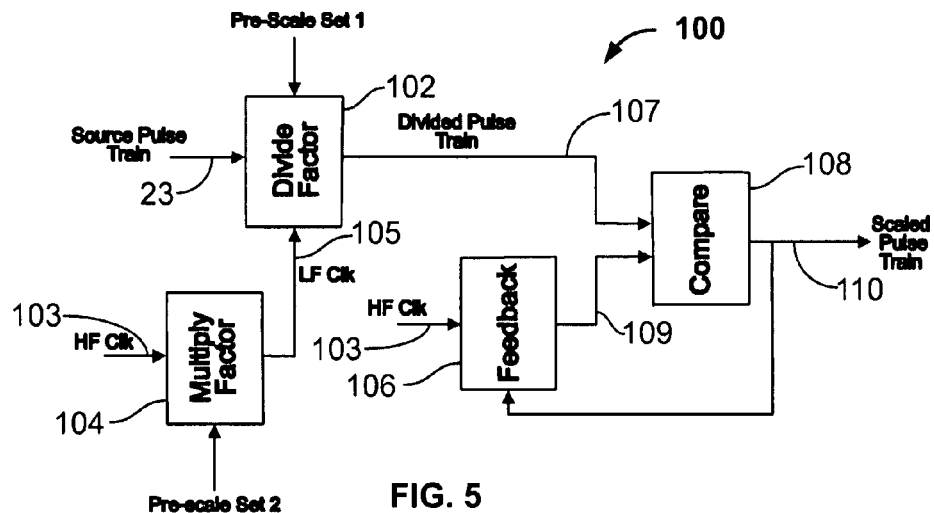
FIG. 5 is a block diagram of the pre-scale module shown in FIG. 3 as utilized in accordance with an embodiment of the present invention.

At 406, the encoder signal 23 may be input to the Pre-scaler module 62. FIG. 5 illustrates a module diagram 100 of the Pre-Scaler module 62 used in accordance with an embodiment of the invention. The Pre-Scaler module 62 includes a divide factor component 102, a multiply factor component 104, a feedback element 106, and a compare component 108.

The divide factor 102 implements a transfer function. In one embodiment, the transfer function is determined by the following equation:

Output=(input signal/Pre-Scale Set 1)*Pre-Scale Set 2, where "input signal" is the scaled encoder input, "Pre-Scale Set 1" is a user selected factor used to divide the scaled encoder input, and "Pre-Scale Set 2" is a user selected value to lower the system clock frequency (e.g., shown as HF clk 103) in order to perform the multiply.

The division portion of the transfer function (e.g., (input signal/pre-scale set 1)) may be performed using the divide factor 102, for example, implemented as a counter. The divide factor 102 may divide the encoder signal 23 based on a user selected value, (e.g., a factor of two, five, ten, one-hundred, and the like). The multiplication portion of the transfer function may be performed in real-time and implemented by the compare component 108. The compare component 108 compares a count from the divided pulse train 107 with a count 109 from the feedback element 106. A pulse is generated when the count 109 is equal to the count 107 from the divided pulse train. The generated pulse effectively multiplies the divided pulse train 107 by the Pre-Scale Set 2 value. Multiplying by the Pre-Scale Set 2 value may not be utilized, and may be used when necessary to attain a specific target frequency.

Figure 6:
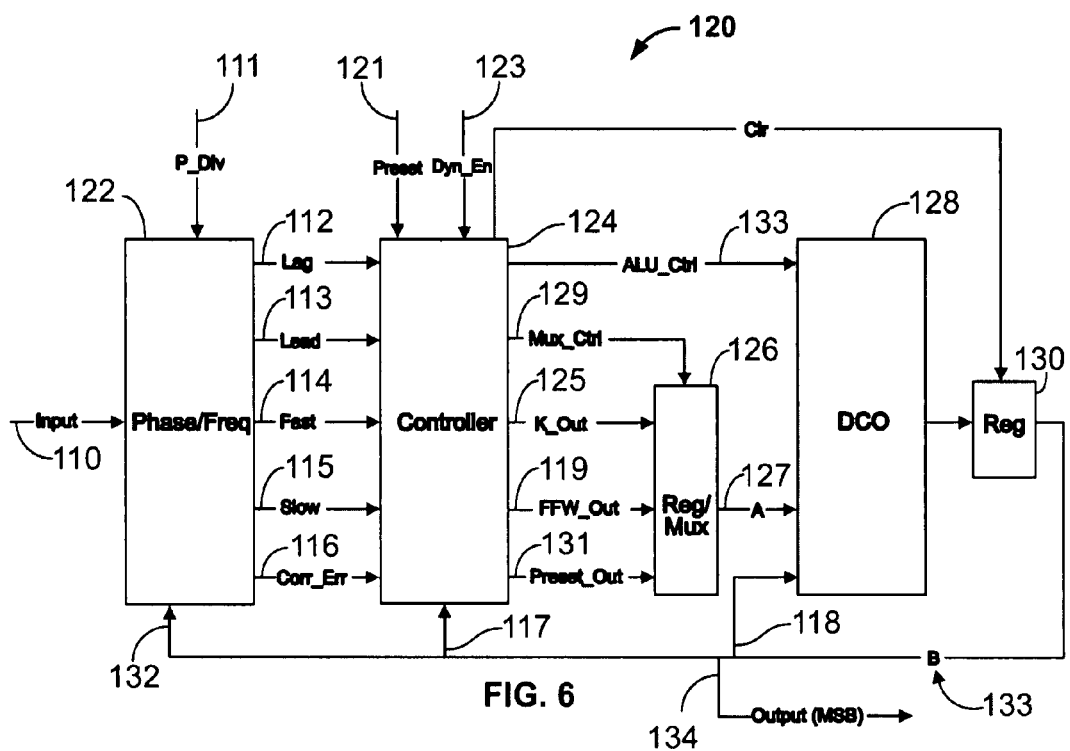
FIG. 6 is a block diagram of a digital phase locked loop (DPLL) shown in FIG. 3 utilized in accordance with an embodiment of the present invention.

Returning to FIG. 4, at 408, the scaled pulse train 110 is input to the DPLL 64 (shown in FIG. 3). FIG. 6 illustrates a detailed block diagram 120 of the DPLL 64 constructed in accordance with an embodiment of the invention. The DPLL 64 may be configured as a field programmable gate array (FPGA), an application specific integrated circuit (ASIC), constructed from discrete logic, and the like. As shown in FIG. 6, the DPLL 64 includes a phase/frequency (phase/freq) component 122, a controller 124, a multiplexer (Reg/Mux) 126, a digital controlled oscillator (DCO) 128 and a register 130 (e.g., Reg). The phase/freq component 122 accepts the following as input: the scaled pulse train 110 and a value 111 (e.g., P_Div) to divide the output of PLL represented as a feedback signal 132 from bus B 133. The phase/freq component 122 may be a phase detector that detects differences in phase between the input signal 110 and the output signal 132. Alternatively, the phase/freq component 122 may be a state machine that determines which of the two signals 110, 132 has a zero-crossing earlier or more often. For example, the phase/freq component 122 compares the output signal 132 with the inputs signal 110 to determine a correction between the output signal 132 and the input signal 110. For instance, compared to the output signal 132, the input signal 110 may lag, lead, be too fast, or be too slow. A correction may be provided by the phase/frequency component 122. For instance, an error correction signal 116 (e.g., Corr_Err) may be generated along with a signal indicating how to correct for a lag 112, a lead 113, a fast signal 114, or a slow signal 115. The error correction signal 116 (e.g., Corr_Err) along with the lag 112, lead 113, fast 114, and slow 115 signal may be used by the controller 124 to add or subtract a value from the DCO 128. The correction error signal 116 may indicate an amount of correction required to increase convergence speed to a desired output signal.

Returning to FIG. 4, at 410, the changed output signal value 132 may command the data acquisition system to capture at a new frequency corresponding to change in gantry speed. At 412, the DPLL 120 output signal 132 may be corrected by selecting a linear correction method. For instance, the controller 124 (shown in FIG. 6) may accept a current value 117 from the DCO 128 (e.g., an accumulator) that may be fed back from the output signal 132. The current value 117 together with the error correction signal (e.g., lag 112, lead 113, fast 114, slow 115, and the like) provided by the phase/freq module 122, a new accumulator value may be generated (e.g., K_Out 125).

Alternatively, the correction error may be a non-linear correction that may be used to "inject a seed value" to rapidly lock the output signal 132 to a desired value. For example, the controller 124 may accept a dynamic enable signal 123 (Dyn_En) having a "high value" (e.g., a one) to accept a seed value. When the dynamic enable signal 123 changes states from a zero to a one, a non-linear correction mode may be selected (e.g., Corr_Err 116 value is set to a correction amount), and the signal 116 latches into controller 124 the correction value. The Corr_Err value is "injected" as the seed value into controller 123 to force the output signal 132 to rapidly approach the desired value, which may be based on a Preset signal 121. Thus, when dynamically latching a correction value using the non-linear operation mode, the seed value may be output from controller 124 on signal line FFW_Out 119. Optionally, the correction value may be output on the K_out 125 signal line if the multiplexer 126 is implemented in the controller block.

The multiplexer 126 may accept the new accumulator value, K_Out 125. The multiplexer 126 may select a value to linearly correct the output signal 132. Alternatively, the multiplexer 126 may select a correction value (e.g., a non-linear convergence mode), when a seed value is used, to narrow the difference of the output signal to a desired output signal value. The multiplexer control line (Mux_Ctrl) 129 selects which correction value to use, for example, the seed value on the FFW_Out 119 signal line or the linear correction on the K_Out 125 signal line. Alternatively, when a new value for the output signal 132 is desired (e.g., after a change in rotational speed), the Mux_Ctrl line 129 selects the Preset_Out line 131, which may change the output signal 132 to lock to a new trigger frequency for accurate projection collection triggers at the new speed.

A change in the DCO 129 accumulator value may be implemented by the values of the K_Out 125 signal line. For instance, the value of the K_Out 125 signal line may be added to the DCO 128 accumulator value. Alternatively, the value of K_Out 125 signal line may be subtracted from the DCO 129 accumulator value. The selected value 127 may be input to the DCO 128 along with a feedback signal 118. For instance, the ALU_Ctrl line 133 may instruct the DCO 128 to add or subtract data from the selected value 127 signal line from the feedback signal 118, which may result in changing the speed of the output signal 132.

The DCO 128 outputs a digital signal that may be wide enough to provide sufficient correction resolution to the Register 130. The DCO 128 functions as an accumulator, and adjusts the output signal 132 by adding or subtracting an adjustment (controlled by the ALU_Ctrl line 133). When the DCO 128 overflows, a most-significant bit (MSB) changes states (e.g., from a zero to a one). The value of the MSB may be output 134.

Returning to FIG. 4, at 412, when the output signal value 132 equals a desired value, no more adjustments are necessary. Therefore, at 414, the DPLL 120 is locked at the desired value.

Figure 7:
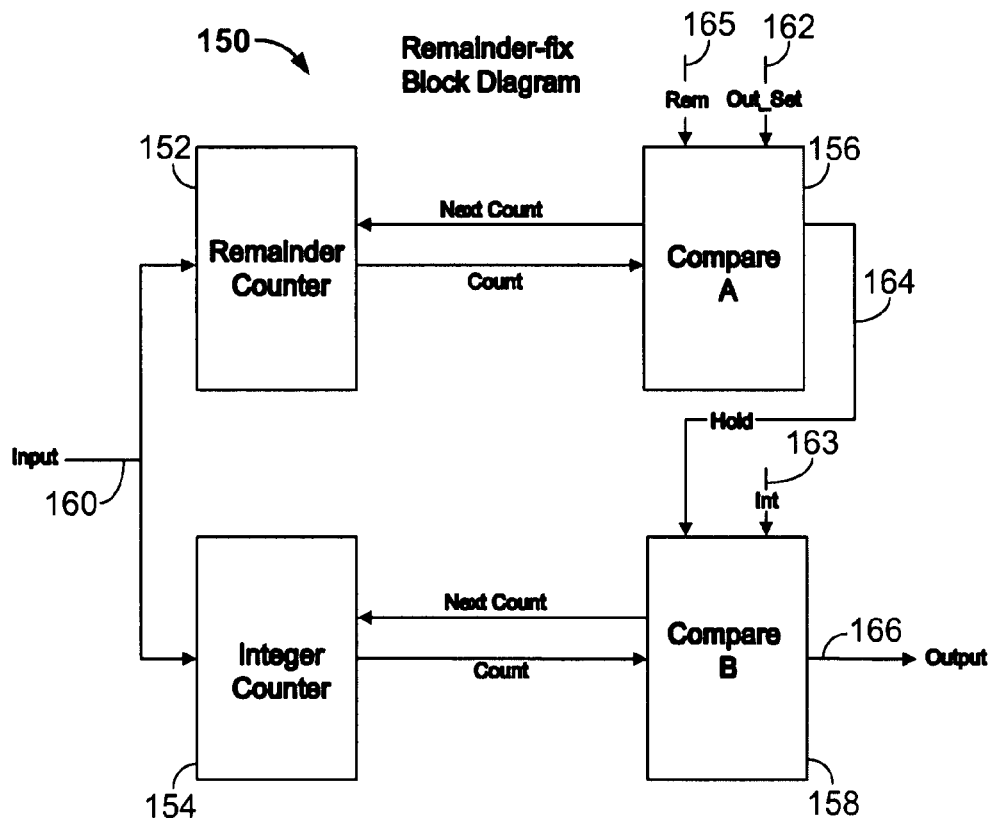
FIG. 7 is a block diagram of the remainder-fix module shown in FIG. 3 utilized in accordance with an embodiment of the present invention.

At 416, a remainder may be determined that may be accumulated and then added to a pulse. FIG. 7 illustrates a block diagram 150 of the remainder-fix module 66 shown in FIG. 3 utilized in accordance with an embodiment of the present invention. The remainder-fix module 66 enables an arbitrary number of encoder pulses 160 to generate output triggers 166. The remainder-fix module 66 includes a remainder counter 152, an integer counter 154, a compare A element 156 and a compare B element 158. The remainder-fix module 66 accepts pulses from the DPLL 64 on the input line 160. The remainder-fix module 66 implements a function: (number of PLL pulses per revolution/desired number of output pulses per revolution). Further, the remainder-fix module 66 accepts values for Rem 165, Out_Set 162, and Int 163, for example, from a processor external to the imaging system 10. The Rem 165 may represent a numerator of a non-integer remainder of the transfer function, Out_Set 162 may represent a denominator of a non-integer remainder of the transfer function, and Int may represent an integer portion of the transfer function.

An exemplary example of the remainder-fix module 66 is described below. For instance, the PLL may input 10,000 pulse per rotation, a desired number of output pulses may be set to 984/rotation, the Rem 165 may be set to 20, Out_Set 162 may be set to 123, and Int 163 may be set to 10. The remainder counter 152 may use the value of Rem 165 to increment a "rem_count." The integer counter 154 may be incremented by a value of one for each input pulse entered on input 160. After the first six input pulses, the integer counter 154 has a value of 6 (e.g., Int_count=6), and the remainder counter 152 has a value of 120 (e.g., rem_count=6*20=120).

On the seventh input pulse, the rem_count (e.g., rem_count=7*20=140) is greater than the value of Out_Set 162 (e.g., 140>132). When the rem_count value exceeds the Out_Set 162 value, the value of rem_count may be adjusted according to: rem_count=rem_count−Out_Set (e.g., rem_count=17). In addition, the hold signal 164 may be asserted to stop the integer counter 154 from incrementing (e.g., Int_count remains at the last value, for instance, Int_count=6). Thus, while the hold signal 164 is asserted, the integer counter 154 is prevented from incrementing. The arrival of the next pulse may de-assert the hold signal 164.

For each of the following input pulses 160, both the integer counter 154 and the remainder counter 152 are incremented. For instance, on the eighth pulse, the integer counter 154 is incremented by a value of one, such that Int_count=7, and the remainder counter 152 (e.g., rem_count=17) is incremented by the value of rem 165 (e.g., 20), such that rem_count=37. When the value of Int_count equals the value of Int 163 (e.g., 10), an output pulse 166 is generated and the value of the integer counter is cleared (e.g., int_count=0). For example, on the 11$^{th}$ input pulse, Int_count=0 and rem_count=97. On the 13$^{th}$ input pulse, rem_count (e.g., value of 137) has a value greater than Out_Set 162 (e.g., 123), which causes the hold signal 164 to be asserted and the value of rem_count to be adjusted (e.g., rem_count=rem_count−Out_Set=137−123=15). The process repeats until output 166 has provided 984 pulses.

Returning to FIG. 4, at 418, the value of the remainder may be spread over a plurality of encoder pulses. For example, in FIG. 7, the Hold signal 164 may be used to determine when a predetermined amount of a remainder value has accumulated to add to a pulse. Thus, by using the remainder-fix module 150, an arbitrary number of encodes pulses may generate triggers for an arbitrary number of images to be acquired per gantry rotation with each image evenly spaced from each other. For example, the output 166 may have a value for a number of desired pulses per gantry rotation for an arbitrary input 160 pulse count.

Figure 8:
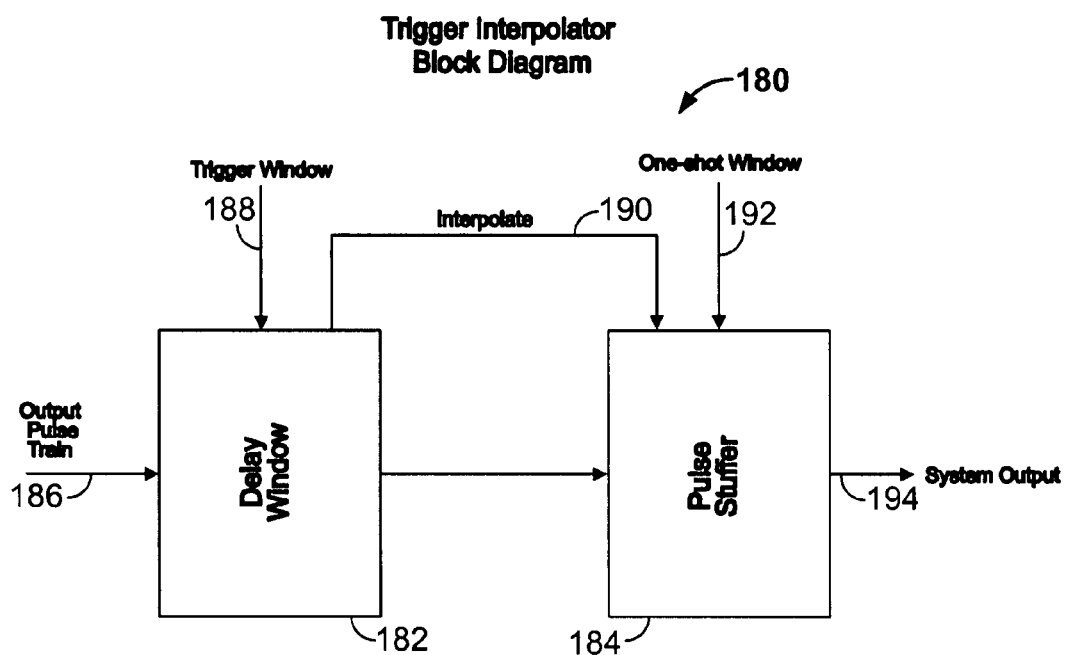
FIG. 8 is a block diagram of the trigger interpolator module shown in FIG. 3 utilized in accordance with an embodiment of the present invention.

Optionally, a trigger interpolator may be utilized to reduce scan failure from failed inputs to the DPLL 120 (shown in FIG. 6). Returning to FIG. 4, at 420 a trigger pulse may be injected in real-time when an input to the DPLL 120 fails. The failure may be the result of noise, a communication error, an intermittent error, an instantaneous error, and the like. FIG. 8 illustrates a block diagram of a trigger interpolator 180 (shown in FIG. 3) utilized in accordance with an embodiment of the present invention. The trigger interpolator 180 includes a delay window 182 and a pulse stuffer 184. A pulse train 186 is input to the delay window, where the pulse train 186 may include a failure, such as a missed pulse. A trigger window 188 provides a value for a window for an expected pulse. A one shot trigger is generated on an interpolate signal 190 and input to the pulse stuffer 184. A one-shot window 192 provides an ignore time period from Register 130 (shown in FIG. 6). The ignore time allows a period of time for a signal to be held to avoid a double trigger. The interpolated signal 194 may be provided at a desired frequency value. The trigger interpolator 180 may be implemented in software. Alternatively, the trigger interpolator 180 may be implemented in hardware.

A technical effect of the various embodiments is to use a diagnostic or baggage imaging system, such as a computed tomography (CT) imaging system having a digital phase locked loop for multiplying and filtering encoder generated data acquisition signal (DAS) triggers to provide a predetermined number of pulses per gantry rotation. The digital phase locked loop may be injected with a desired frequency to quickly generate a desired output signal with minimal jitter.

The various embodiments or components thereof may be implemented as part of a computer system. The computer system may include a computer, an input device, a display unit, and an interface, for example, for accessing the Internet. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

In various embodiments of the invention, the method of creating a CT attenuation correction image as described herein or any of its components may be embodied in the form of a processing machine. Typical examples of a processing machine include a general-purpose computer, a programmed microprocessor, a digital signal processor (DSP), a microcontroller, a peripheral integrated circuit element, and other devices or arrangements of devices, which are capable of implementing the steps that constitute the methods described herein.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The processing machine executes a set of instructions (e.g., corresponding to the method steps described herein) that are stored in one or more storage elements (also referred to as computer usable medium). The storage element may be in the form of a database or a physical memory element present in the processing machine. The storage elements may also hold data or other information as desired or needed. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a Hard Disc Drive (HDD) and a compact disc read-only memory (CDROM). The above memory types are exemplary only, and are thus limiting as to the types of memory usable for storage of a computer program.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

In various embodiments of the invention, the method of creating can be implemented in software, hardware, or a combination thereof. The methods provided by various embodiments of the present invention, for example, can be implemented in software by using standard programming languages such as, for example, C, C++, Java, and the like. As used herein, the terms "software" and "firmware" are interchangeable, and include any computer program stored in memory for execution by a computer.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method of minimizing output pulse jitters in a digital phase locked loop, the method comprising:
    pre-setting the digital phase locked loop to a predetermined frequency based on a preset value received at a preset input;
    latching the preset value to change a frequency of an output signal; and
    locking the digital phase locked loop to the latched frequency.

2. The method of claim 1, wherein the pre-setting comprises latching in a seed value into an accumulator of a digital controlled oscillator (DCO) to correct the output signal.

3. The method of claim 1, wherein pre-setting comprises selecting a frequency value to minimize a difference between the phase locked loop output signal and a predetermined value.

4. The method of claim 1, further comprising pre-scaling a pulse train to form a scaled pulse train by dividing a plurality of pulses by a predetermined value.

5. The method of claim 1, wherein locking comprises producing an arbitrary number of output pulses for a given number of input pulses.

6. The method of claim 1, wherein locking comprises:
    (i) turning-off a digital filter until the digital phase locked loop has locked to the predetermined frequency to generate an output signal; and
    (ii) turning-on a digital filter after the digital phase locked loop has locked to the predetermined frequency, the digital filter enabled to filter jitter from an output signal.

7. The method of claim 1, further comprising interpolating a trigger in real-time when an input trigger event to the phase locked loop fails, the failure resulting from at least one of noise, a communication error, an intermittent error, an instantaneous error, and the phase locked loop not receiving an encoder pulse.

8. The method of claim 1, further comprising interpolating a trigger by determining a trigger value to continue a scan, the trigger value based on at least one of a frequency of previously generated digital acquisition triggers and a history of generated encoder pulses over a predetermined period of time.

9. The method of claim 1, further comprising interpolating a trigger to continue a scan when an input trigger event is missed.

10. The method of claim 1, further comprising multiplying an encoder input signal by a preselected value to sample the input signal at a preselected frequency.

11. The method of claim 1, further comprising spreading a remainder over a plurality of pulses, the remainder determined by dividing an encoder input value by a desired output value.

12. The method of claim 1, further comprising controlling a speed of a motor using the output signal.

13. The method of claim 12, wherein the motor is connected to a rotatable gantry and the pre-setting is based on a change in a speed of the motor.

14. The method of claim 13, wherein the rotatable gantry comprises a computed-tomography gantry.

15. The method of claim 1, further comprising receiving as an input signal a scaled pulse train at an input of the digital phase locked loop and receiving the pre-set value at the preset input of a controller of the digital phase locked loop.

16. The method of claim 1, wherein the preset value is received separate from an input signal of a scaled pulse train, wherein only the frequency of the output signal is changed based on the preset and not the input signal.

17. The method of claim 1, further comprising generating the preset value as a preset signal using a processor external to the digital phase locked loop and using the preset value to seed a change in a trigger output frequency of the output signal different than a current value from a digital controlled oscillator providing a feedback signal.

* * * * *